US010056850B2

(12) United States Patent
Meloche et al.

(10) Patent No.: US 10,056,850 B2
(45) Date of Patent: Aug. 21, 2018

(54) WEARABLE POWER GENERATING DEVICE

(71) Applicants: Joseph L. Meloche, Rochester Hills, MI (US); Heather S. Meloche, Rochester Hills, MI (US)

(72) Inventors: Joseph L. Meloche, Rochester Hills, MI (US); Heather S. Meloche, Rochester Hills, MI (US)

( * ) Notice: Subject to any disclaimer, the term of this patent is extended or adjusted under 35 U.S.C. 154(b) by 347 days.

(21) Appl. No.: 15/045,459

(22) Filed: Feb. 17, 2016

(65) Prior Publication Data
US 2017/0104425 A1 Apr. 13, 2017

Related U.S. Application Data

(60) Provisional application No. 62/240,052, filed on Oct. 12, 2015.

(51) Int. Cl.
| H02N 2/18 | (2006.01) |
| H01L 41/113 | (2006.01) |
| A61B 5/00 | (2006.01) |
| A61B 5/024 | (2006.01) |
| A61B 5/145 | (2006.01) |
| A61B 5/01 | (2006.01) |

(52) U.S. Cl.
CPC ............. *H02N 2/181* (2013.01); *A61B 5/01* (2013.01); *A61B 5/024* (2013.01); *A61B 5/14542* (2013.01); *A61B 5/681* (2013.01); *A61B 5/742* (2013.01); *H01L 41/1132* (2013.01); *A61B 2560/0214* (2013.01)

(58) Field of Classification Search
CPC ....................................................... H02N 2/18
See application file for complete search history.

(56) References Cited

U.S. PATENT DOCUMENTS

| 5,918,502 | A | * | 7/1999 | Bishop | A43B 3/0005 36/136 |
| 8,827,930 | B2 | * | 9/2014 | Wekell | A61B 5/0002 600/587 |
| 9,581,972 | B1 | * | 2/2017 | Arrow | H01M 10/46 |
| 9,869,807 | B2 | * | 1/2018 | Kim | G02B 6/0041 |
| 2010/0090477 | A1 | * | 4/2010 | Keating | A43B 3/0005 290/1 R |
| 2010/0127967 | A1 | * | 5/2010 | Graumann | H02N 2/183 345/156 |
| 2013/0257219 | A1 | * | 10/2013 | Monfray | H02N 2/18 310/306 |
| 2013/0280549 | A1 | * | 10/2013 | Monfray | H02N 2/18 428/603 |

(Continued)

*Primary Examiner* — J. San Martin
(74) *Attorney, Agent, or Firm* — Buckert Patent & Trademark Law Firm PC; John F. Buckert

(57) ABSTRACT

A wearable power generating device is provided. The wearable power generating device includes an arcuate-shaped flexible substrate, a first energy generating device, an energy harvesting circuit, and an energy storage device. The first energy generating device generates a first voltage in response to the first energy generating device being in tension or compression or being bent. The energy harvesting circuit receives the first voltage and outputs a DC voltage in response to receiving the first voltage. The energy storage device is electrically coupled to the energy harvesting circuit and receives the DC voltage.

20 Claims, 4 Drawing Sheets

(56) References Cited

U.S. PATENT DOCUMENTS

| | | | |
|---|---|---|---|
| 2015/0229237 A1* | 8/2015 | Davis | A45F 5/02 |
| | | | 224/581 |
| 2015/0250418 A1* | 9/2015 | Ashby | A61B 5/0002 |
| | | | 600/474 |
| 2016/0023245 A1* | 1/2016 | Zadesky | A61B 5/7455 |
| | | | 310/334 |
| 2016/0058133 A1* | 3/2016 | Fournier | H04B 1/3888 |
| | | | 455/41.2 |
| 2016/0282899 A1* | 9/2016 | Inagaki | G04G 9/04 |
| 2016/0349790 A1* | 12/2016 | Connor | G06F 1/1694 |
| 2017/0040306 A1* | 2/2017 | Kim | H01L 25/167 |
| 2017/0045958 A1* | 2/2017 | Battlogg | A61F 2/38 |
| 2017/0054318 A1* | 2/2017 | Matsuyuki | H01L 23/5226 |
| 2017/0086672 A1* | 3/2017 | Tran | A61B 5/0022 |
| 2017/0120107 A1* | 5/2017 | Wisbey | G09B 19/00 |
| 2017/0135633 A1* | 5/2017 | Connor | A61B 5/4836 |
| 2017/0164878 A1* | 6/2017 | Connor | A61B 5/14532 |
| 2017/0265753 A1* | 9/2017 | Baek | A61B 5/021 |
| 2017/0324022 A1* | 11/2017 | Ting | H01L 41/113 |
| 2017/0340049 A1* | 11/2017 | Rice | A43B 13/386 |
| 2018/0039232 A1* | 2/2018 | Abramov | G04B 47/00 |
| 2018/0084324 A1* | 3/2018 | Vitt | H04R 1/026 |

* cited by examiner

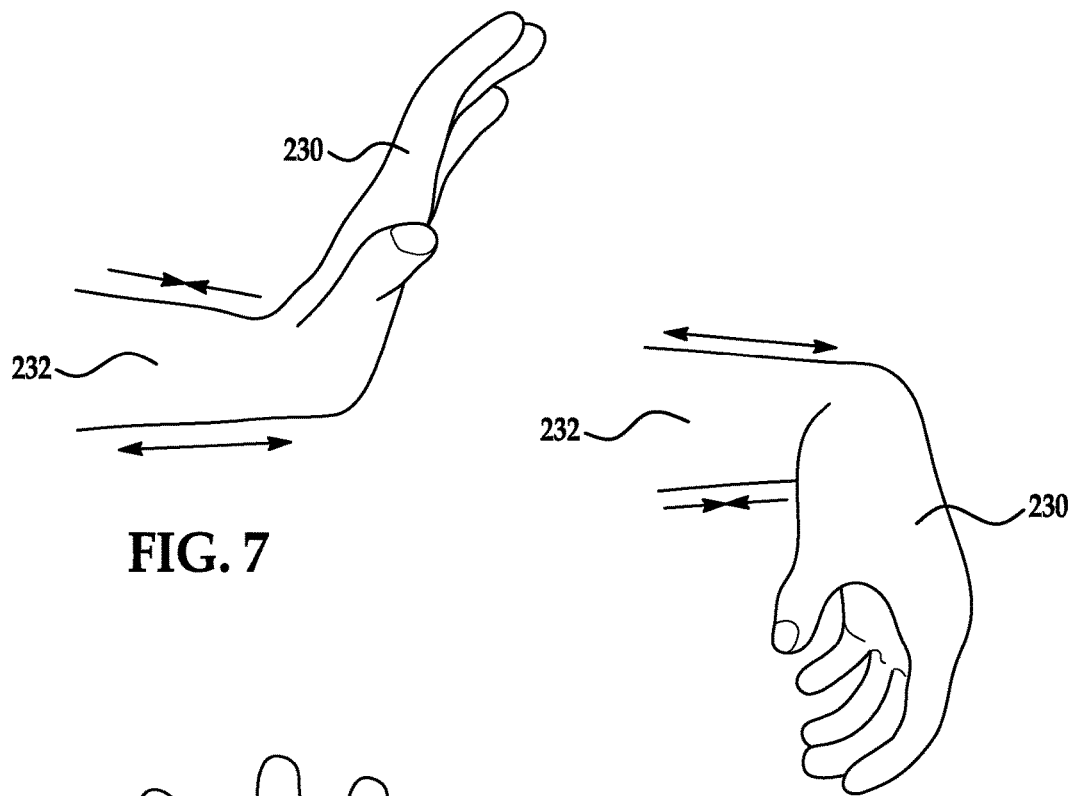
FIG. 7
FIG. 8
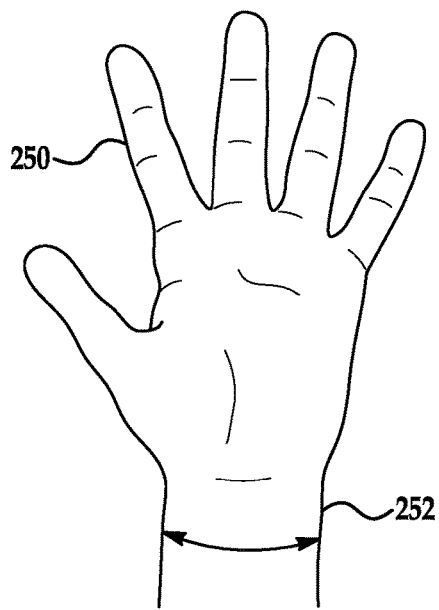
FIG. 9
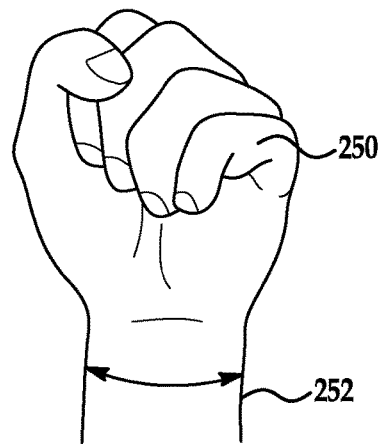
FIG. 10

WEARABLE POWER GENERATING DEVICE

CROSS-REFERENCE TO RELATED APPLICATION

This application claims priority to U.S. Provisional Patent Application No. 62/240,052 filed on Oct. 12, 2015, the entire contents of which are hereby incorporated by reference herein.

BACKGROUND

The inventors herein have recognized a need for a wearable power generating device.

SUMMARY

A wearable power generating device in accordance with an exemplary embodiment is provided. The wearable power generating device includes an arcuate-shaped flexible substrate. The wearable power generating device further includes a first energy generating device that is disposed on and coupled to the arcuate-shaped flexible substrate that generates a first voltage in response to the first energy generating device being in tension or compression or in response to the first energy generating device being bent. The wearable power generating device further includes an energy harvesting circuit that is disposed on and coupled to the arcuate-shaped flexible substrate. The energy harvesting circuit is electrically coupled to the first energy generating device. The energy harvesting circuit receives the first voltage from the first energy generating device and outputs a DC voltage in response to receiving the first voltage. The wearable power generating device further includes an energy storage device that is electrically coupled to the energy harvesting circuit and receives the DC voltage.

BRIEF DESCRIPTION OF THE DRAWINGS

FIG. 7 is a schematic of a hand and a wrist in a first anatomical position wherein a top portion of the wrist is under compression and a bottom portion of the wrist is under tension;

FIG. 8 is a schematic of a hand and a wrist in a second anatomical position wherein a top portion of the wrist is under tension and a bottom portion of the wrist is under compression;

FIG. 9 is a schematic of a hand and a wrist in a third anatomical position wherein a bottom portion of the wrist is under tension; and FIG. 10 is a schematic of a hand and a wrist in a fourth anatomical position wherein a bottom portion of the wrist is under tension.

DETAILED DESCRIPTION

Figure 1:
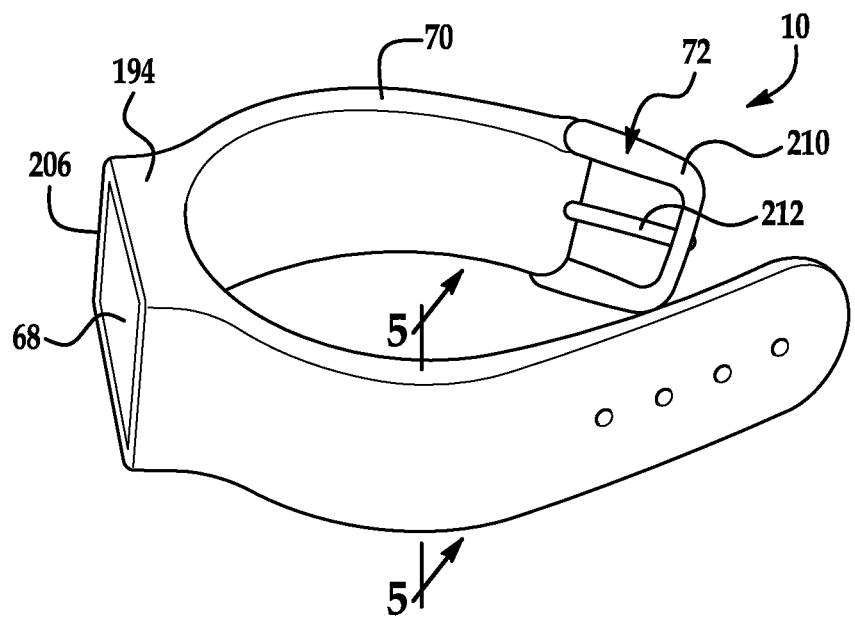
FIG. 1 is a schematic of a wearable power generating device in accordance with an exemplary embodiment.

Referring to FIGS. 1-6, a wearable power generating device 10 in accordance with an exemplary embodiment is provided. The wearable power generating device 10 includes an arcuate-shaped flexible substrate 20, energy generating devices 30, 32, 34, 36, an energy harvesting circuit 50, an energy storage device 60, a microprocessor 64, a biometric sensor 66, a display device 68, an external case 70, and a fastener assembly 72. An advantage of the wearable power generating device 10 is that the device 10 generates a DC voltage in response to energy generating device being in tension or compression or bent on a user's wrist to charge the energy storage device 60 and to provide electrical power for the microprocessor 64, the biometric sensor 66, and the display device 68.

In an exemplary embodiment, the energy generating devices 30, 32, 34, 36 are piezo-electric devices. In an alternative embodiment, the energy generating devices 30, 32, 34, 36 are dielectric elastomer devices. However, for purposes of simplicity, the energy generating devices 30, 32, 34, 36 will be described as piezo-electric devices hereinafter. Further, it should be understood that for the alternative embodiment using dielectric elastomer devices instead of piezo-electric devices, one could replace each instance of the words "piezo-electric device" with the words "dielectric elastomer device" hereinafter to enable such an embodiment.

Figure 2:
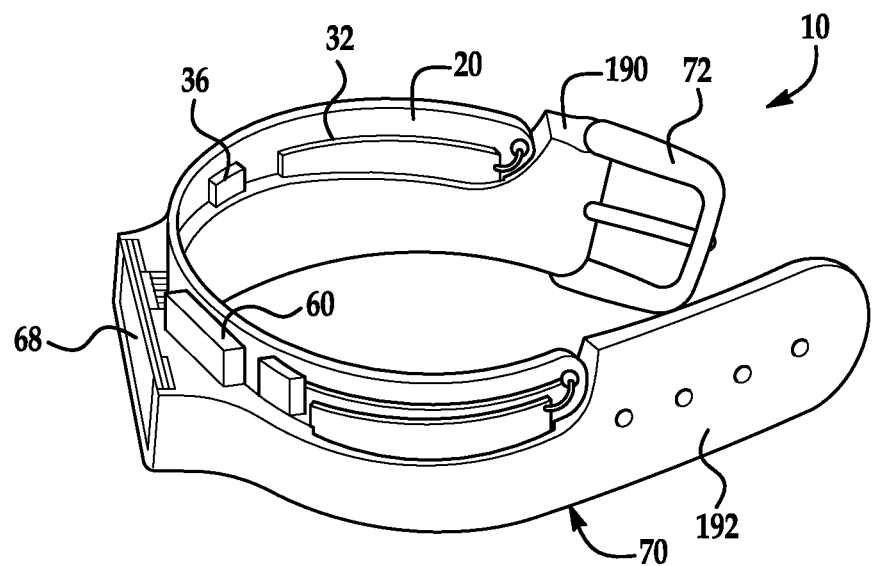
FIG. 2 is a schematic of the wearable power generating device of FIG. 1 with a portion of an external case removed therefrom.
Figure 3:
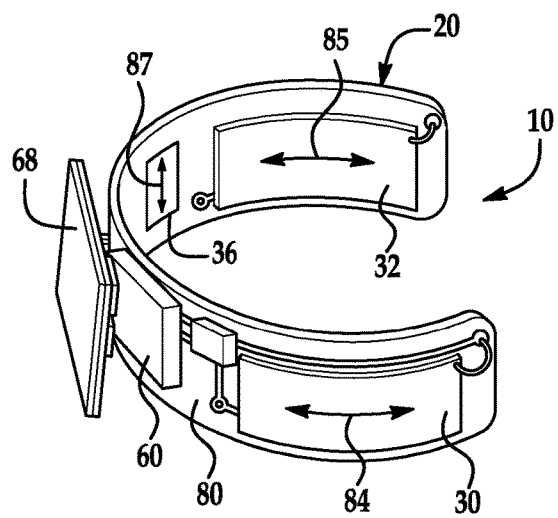
FIG. 3 is a schematic of an arcuate-shaped flexible substrate and components thereon that are utilized in the wearable power generating device of FIG. 1.

Referring to FIGS. 2 and 3, the arcuate-shaped flexible substrate 20 is provided to hold the other components of the wearable power generating device 10 thereon. The arcuate-shaped flexible substrate 20 has a first side 80 and a second side 82, and the substrate 20 is sized and shaped to wrap around a portion of the user's wrist. In an exemplary embodiment, the arcuate-shaped flexible substrate 20 is constructed of a ceramic material or circuit board material. In an alternative embodiment, the arcuate-shaped flexible substrate 20 is constructed of a plastic material or a flexible metal. Of course, in other alternative embodiments, the arcuate-shaped flexible substrate 20 could be constructed of other materials having sufficient flexibility properties.

Figure 6:
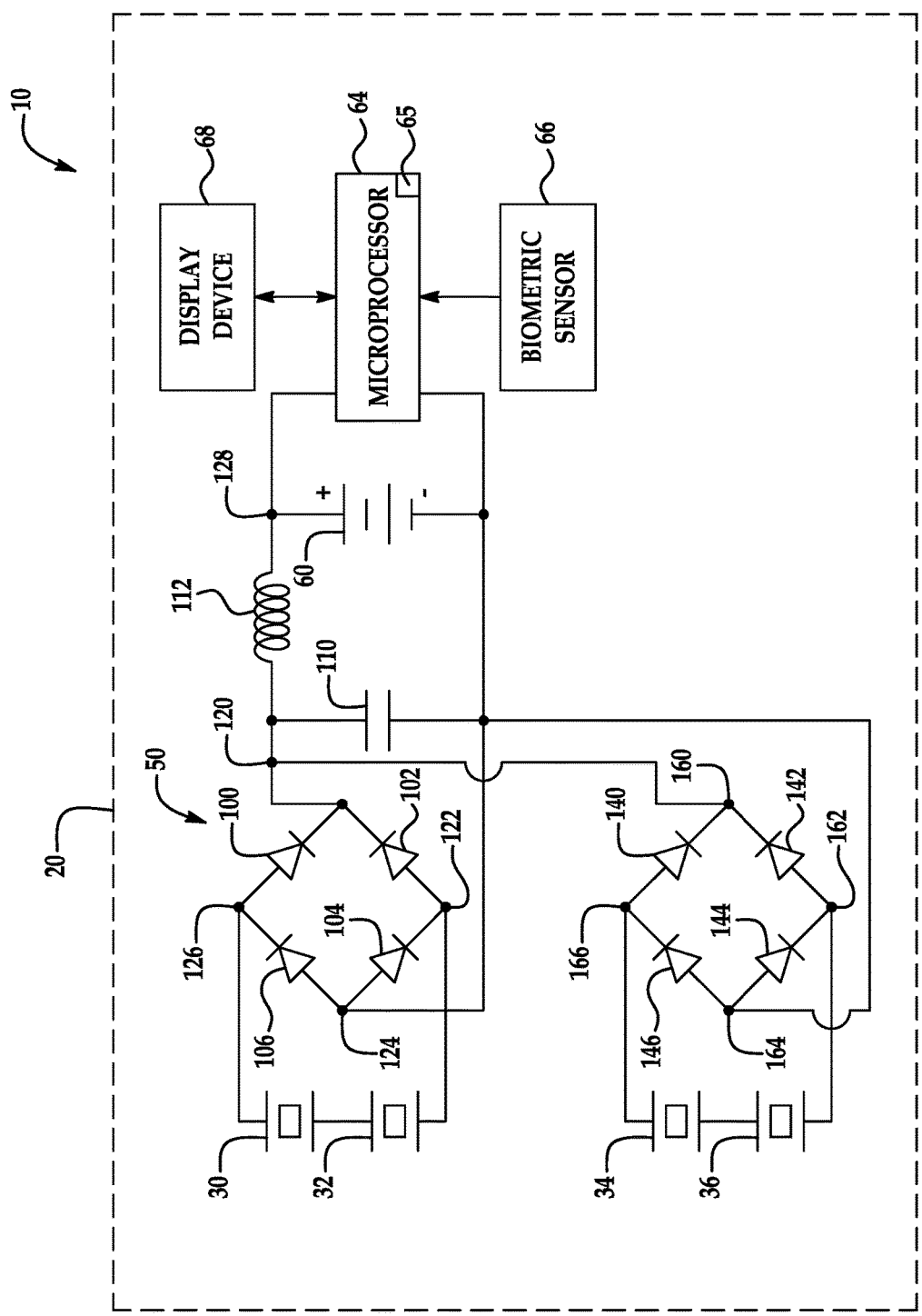
FIG. 6 is a schematic of an electrical circuit utilized in the wearable power generating device of FIG. 1.

Referring to FIGS. 3 and 6, the piezo-electric device 30 is disposed on and coupled to the first side 80 of the arcuate-shaped flexible substrate 20 and generates a voltage in response to the piezo-electric device 30 being in tension or compression along a longitudinal axis 84 or in response to the piezo-electric device 30 being bent. The piezo-electric device 30 is electrically coupled in series with the piezo-electric device 32. The piezo-electric device 30 is in tension or compression along the longitudinal axis 84 based on anatomical position of a wrist and a hand of the user, when the wearable power generating device 10 is disposed on the wrist of the user. For example, referring to FIGS. 9 and 10, when the wearable power generating device 10 is disposed on the wrist of the user, the piezo-electric device 30 would be under tension when the fingers of the hand are fully extended (as shown in FIG. 9) or when the fingers of the hand are clenched in a fist (as shown in FIG. 10).

Referring to FIGS. 3 and 6, the piezo-electric device 32 is disposed on and coupled to the second side 82 of the arcuate-shaped flexible substrate 20 and generates a voltage in response to the piezo-electric device 32 being in tension or compression along a longitudinal axis 85 thereof or in response to the piezo-electric device 32 being bent. The piezo-electric device 32 is in tension or compression along the longitudinal axis 85 based on anatomical position of a wrist and a hand of the user, when the wearable power generating device 10 is disposed on the wrist of the user. For example, referring to FIGS. 9 and 10, when the wearable power generating device 10 is disposed on the wrist of the user, the piezo-electric device 32 would be under tension when the fingers of the hand are fully extended (as shown in FIG. 9) or when the fingers of the hand are clenched in a fist (as shown in FIG. 10).

Figure 4:
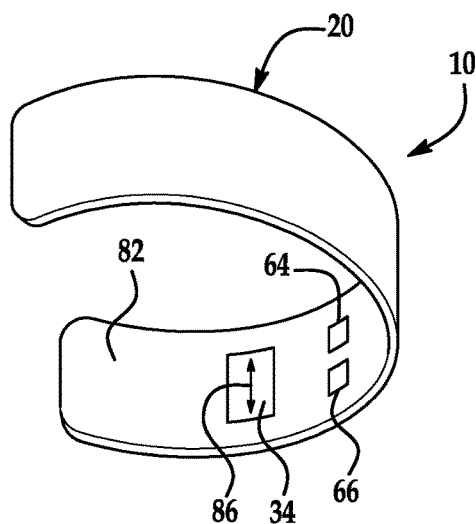
FIG. 4 is a schematic of the arcuate-shaped flexible substrate of FIG. 3.
Figure 5:
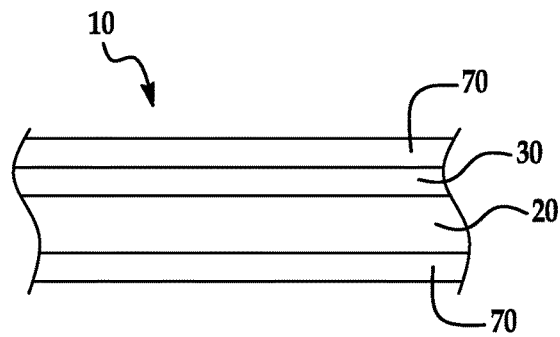
FIG. 5 is a cross-sectional schematic of the wearable power generating device of FIG. 1 taken along lines 5-5.

Referring to FIGS. 4 and 6, the piezo-electric device 34 is disposed on and coupled to the second side 82 of the arcuate-shaped flexible substrate 20 and generates a voltage in response to the piezo-electric device 34 being in tension or compression along a longitudinal axis 86 thereof or in response to the piezo-electric device 34 being bent. The longitudinal axis 86 is substantially perpendicular to the longitudinal axis 84. The piezo-electric device 34 is electrically coupled in series with the piezo-electric device 36. The piezo-electric device 34 is in tension or compression along a longitudinal axis 86 thereof based on anatomical position of a wrist and a hand of the user, when the wearable power generating device 10 is disposed on the wrist of the user. For example, referring to FIGS. 7 and 8, when the wearable power generating device 10 is disposed on the wrist of the user, the piezo-electric device 34 (disposed near the top of the wrist) could be under compression when the fingers of the hand are extended upwardly at an acute angle relative to the wrist (as shown in FIG. 7) or the piezo-electric device 34 could be under tension when the fingers of the hand extend downwardly at a 90 degree angle relative to the wrist (as shown in FIG. 8).

Referring to FIGS. 3 and 6, the piezo-electric device 36 is disposed on and coupled to the second side 82 of the arcuate-shaped flexible substrate 20 and generates a voltage in response to the piezo-electric device 36 being in tension or compression along a longitudinal axis 87 thereof or in response to the piezo-electric device 36 being bent. The longitudinal axis 87 is substantially perpendicular to the longitudinal axis 84. The piezo-electric device 36 is in tension or compression along the longitudinal axis 87 based on anatomical position of a wrist and a hand of the user, when the wearable power generating device 10 is disposed on the wrist of the user. For example, referring to FIGS. 7 and 8, when the wearable power generating device 10 is disposed on the wrist of the user, the piezo-electric device 36 (disposed near the top of the wrist) could be under compression when the fingers of the hand are extended upwardly at an acute angle relative to the wrist (as shown in FIG. 7) or the piezo-electric device 36 could be under tension when the fingers of the hand extend downwardly at a 90 degree angle relative to the wrist (as shown in FIG. 8).

Referring to FIG. 6, the energy harvesting circuit 50 is disposed on and is coupled to the arcuate-shaped flexible substrate 20. The energy harvesting circuit 50 is electrically coupled to the piezo-electric devices 30, 32, 34, 36. The energy harvesting circuit receives one or more voltages output from the piezo-electric devices 30, 32, 34, 36 and outputs a DC voltage in response to receiving the one or more voltages output from the piezo-electric devices 30, 32, 34, 36. In an exemplary embodiment, four piezo-electric devices are utilized. However, in an alternative embodiment, one or more piezo-electric devices could be utilized. The energy harvesting circuit 50 includes diodes 100, 102, 104, 106, a capacitor 110, an inductor 112, electrical nodes 120, 122, 124, 126, diodes 140, 142, 144, 146, and electrical nodes 160, 162, 164, 166.

The piezo-electric devices 30, 32 are electrically coupled in series between the electrical nodes 122, 126. The diode 100 is electrically coupled between the electrical nodes 126, 120, and the diode 102 is electrically coupled between the electrical nodes 120, 122. Further, the diode 104 is electrically coupled between the electrical nodes 122, 124, and the diode 106 is electrically coupled between the electrical nodes 124, 126. The capacitor 110 is electrically coupled between the electrical nodes 120, 124. Finally, the inductor 112 is electrically coupled between the electrical node 120 and the electrical node 128. In an exemplary embodiment, the piezo-electric devices 30, 32 could be replaced with a single piezo-electric device that is electrically coupled between the electrical nodes 122, 126. During operation, the energy harvesting circuit 50 outputs a DC voltage between the electrical nodes 128, 124 that is received by the energy storage device 60 for charging the energy storage device 60.

The piezo-electric devices 34, 36 are electrically coupled in series between the electrical nodes 166, 162. The diode 140 is electrically coupled between the electrical nodes 166, 160, and the diode 142 is electrically coupled between the electrical nodes 160, 162. Further, the diode 144 is electrically coupled between the electrical nodes 162, 164, and the diode 146 is electrically coupled between the electrical nodes 164, 166. In an exemplary embodiment, the piezo-electric devices 34, 36 could be replaced with a single piezo-electric device that is electrically coupled between the electrical nodes 162, 166.

The energy storage device 60 is disposed on and coupled to the arcuate-shaped flexible substrate 20 and receives the DC voltage from the energy harvesting circuit 50. In particular, the energy storage device 60 is electrically coupled between the electrical nodes 128, 124. In an exemplary embodiment, the energy storage device 60 is a battery. In an alternative embodiment, the energy storage device 60 is a capacitor or a super capacitor.

The microprocessor 64 is disposed on and coupled to the arcuate-shaped flexible substrate 20. Further, the microprocessor 64 is electrically coupled to the energy storage device 60. The microprocessor 64 includes a memory 65 for storing software instructions and data for controlling the display device 68 as described below.

The biometric sensor 66 is disposed on and coupled to the arcuate-shaped flexible substrate 20. Also, the biometric sensor 66 is operably coupled to the microprocessor 64. The biometric sensor 66 generates a signal indicative of a biometric parameter level of a user wearing the wearable power generating device 10. In an exemplary embodiment, the biometric sensor 66 is a pulse sensor, and the biometric parameter level is a pulse rate of the user. In another exemplary embodiment, the biometric sensor 66 is an oxygen level sensor, and the biometric parameter level is an oxygen level of the user. In yet another exemplary embodiment, the biometric sensor 66 is a temperature sensor, and the biometric parameter level is a temperature level of the user.

Referring to FIGS. 1 and 6, the display device 68 is disposed on and coupled to the arcuate-shaped flexible substrate 20. The display device 68 is operably coupled to the microprocessor 64. The microprocessor 64 is programmed to generate a display command to induce the display device 68 to display one or more biometric parameter levels of the user. In particular, the display device 68 displays alpha-numeric text or a graph indicating at least one of a pulse rate, an oxygen level, and a temperature level of the user wearing the device 10. At least a portion of the display device 68 extends through an aperture 206 in the external case 70.

Referring to FIGS. 1, 2, 3 and 6, the external case 70 is coupled to and covers the arcuate-shaped flexible substrate 20, the piezo-electric devices 30, 32, 34, 36, the energy harvesting circuit 50, the microprocessor 64, the biometric sensor 66, and a portion of the display device 68. In an exemplary embodiment, the external case 70 is substantially arcuate-shaped and is sized and shaped to be removably attached to a human wrist. Further, in an exemplary embodiment, the external case 70 is constructed of a plastic or a rubber compound.

The external case 70 has a first end portion 190, a second end portion 192, and a central portion 194. The central portion 194 is coupled to and between the first end portion 190 and the second end portion 192. The first end portion 190 has the fastener assembly 72 coupled thereto. The fastener assembly 72 has a substantially rectangular ring-shaped frame 210 and a prong 212 rotatably coupled to the rectangular ring-shaped frame 210. The second end portion 192 has apertures 196, 198, 200, 202 extending therethrough for receiving an end of the prong 212 therein. A portion of the display device 68 extends through the aperture 206 of the central portion 194 such that the user can view alphanumeric text and graphs on the display device 68. In an alternative embodiment, the fastener assembly 72 could be replaced with first and second Velcro straps coupled to the first and second end portions 190, 192 of the external case 70.

In an alternative embodiment, the piezo-electric devices 30, 32, 34, 36, the energy harvesting circuit 50, the energy storage device 60, the microprocessor 64, the biometric sensor 66, and the display device 68 could be disposed directly on and coupled to a separate circuit board (not shown). The separate circuit board (not shown) could be disposed directly on and coupled to the arcuate-shaped flexible substrate 20.

The wearable power generating device provides a substantial advantage over other devices for generating electrical power. In particular, the wearable power generating device generates a DC voltage in response to energy generating devices being in tension or compression or being bent on a user's wrist to charge an internal energy storage device and to provide electrical power for a microprocessor, a biometric sensor, and a display device.

While the claimed invention has been described in detail in connection with only a limited number of embodiments, it should be readily understood that the invention is not limited to such disclosed embodiments. Rather, the claimed invention can be modified to incorporate any number of variations, alterations, substitutions or equivalent arrangements not heretofore described, but which are commensurate with the spirit and scope of the invention. Additionally, while various embodiments of the claimed invention have been described, it is to be understood that aspects of the invention may include only some of the described embodiments. Accordingly, the claimed invention is not to be seen as limited by the foregoing description.

What is claimed is:

1. A wearable power generating device, comprising:
   an arcuate-shaped flexible substrate;
   a first arcuate-shaped piezo-electric device being disposed on and coupled to an outer surface of the arcuate-shaped flexible substrate that generates a first voltage in response to the first arcuate-shaped piezo-electric device being in tension or compression along a first axis;
   an energy harvesting circuit being disposed on and coupled to the outer surface of the arcuate-shaped flexible substrate, the energy harvesting circuit being electrically coupled to the first arcuate-shaped piezo-electric device and receiving the first voltage, the energy harvesting circuit outputting a DC voltage in response to receiving the first voltage; and
   an energy storage device being electrically coupled to the energy harvesting circuit and receiving the DC voltage.

2. The wearable power generating device of claim 1, further comprising a second arcuate-shaped piezo-electric device being disposed on and coupled to the arcuate-shaped flexible substrate that generates a second voltage in response to the second arcuate-shaped piezo-electric device being in tension or compression along a second axis, the second arcuate-shaped piezo-electric device being electrically coupled in series with the first arcuate-shaped piezo-electric device, the energy harvesting circuit being electrically coupled to a series combination of the first and second arcuate-shaped piezo-electric devices.

3. The wearable power generating device of claim 2, wherein the first arcuate-shaped piezo-electric device is a first arcuate-shaped piezo-electric sheet having a uniform cross-sectional thickness, and the second arcuate-shaped piezo-electric device is a second arcuate-shaped piezo-electric sheet having a uniform cross-sectional thickness.

4. The wearable power generating device of claim 1, further comprising an external case that is coupled to and covers the arcuate-shaped flexible substrate, the energy harvesting circuit, and the energy storage device.

5. The wearable power generating device of claim 4, wherein the external case has a first end portion and a second end portion, the first end portion having a fastener assembly coupled thereto, and the second end portion having a plurality of apertures extending therethrough.

6. The wearable power generating device of claim 5, wherein the fastener assembly has a substantially rectangular ring-shaped frame and a prong rotatably coupled to the rectangular ring-shaped frame.

7. The wearable power generating device of claim 4, wherein the external case is sized and shaped such that the external case is attachable to a human wrist.

8. The wearable power generating device of claim 1, further comprising:
   a microprocessor being disposed on and coupled to the arcuate-shaped flexible substrate, the microprocessor being electrically coupled to the energy storage device;
   a biometric sensor being disposed on and coupled to the arcuate-shaped flexible substrate, the biometric sensor being operably coupled to the microprocessor, the biometric sensor generating a second signal indicative of a biometric parameter level of a user; and
   a display device being disposed on and coupled to the arcuate-shaped flexible substrate, the display device being operably coupled to the microprocessor, the microprocessor being programmed to generating a display command to induce the display device to display the biometric parameter level.

9. The wearable power generating device of claim 8, wherein the biometric sensor comprises a pulse sensor, and the biometric parameter level is a pulse rate of the user.

10. The wearable power generating device of claim 8, wherein the biometric sensor comprises an oxygen level sensor, and the biometric parameter level is an oxygen level of the user.

11. The wearable power generating device of claim 8, wherein the biometric sensor comprises a temperature sensor, and the biometric parameter level is a temperature level of the user.

12. The wearable power generating device of claim 1, wherein the energy storage device is disposed on and coupled to the arcuate-shaped flexible substrate.

13. The wearable power generating device of claim 2, wherein the first axis is a first curved axis, and the second axis is a second curved axis.

14. The wearable power generating device of claim 2, further comprising a third arcuate-shaped piezo-electric device being disposed on and coupled to the arcuate-shaped flexible substrate that generates a third voltage in response to the third arcuate-shaped piezo-electric device being in tension or compression along a third axis, the third arcuate-shaped piezo-electric device being electrically coupled to the energy harvesting circuit, the third axis being perpendicular to the first axis.

15. The wearable power generating device of claim 2, wherein the first arcuate-shaped piezo-electric device has a uniform cross-sectional thickness.

16. A wearable power generating device, comprising:
an arcuate-shaped flexible substrate;
a first arcuate-shaped piezo-electric device being disposed on and coupled to an outer surface of the arcuate-shaped flexible substrate that generates a first voltage in response to the first arcuate-shaped piezo-electric device being in tension or compression along a first axis; the first arcuate-shaped piezo-electric device having a uniform cross-sectional thickness;
a second arcuate-shaped piezo-electric device being disposed on and coupled to the arcuate-shaped flexible substrate that generates a second voltage in response to the second arcuate-shaped piezo-electric device being in tension or compression along a second axis, the second axis being perpendicular to the first axis; the second arcuate-shaped piezo-electric device having a uniform cross-sectional thickness;
an energy harvesting circuit being disposed on and coupled to the outer surface of the arcuate-shaped flexible substrate, the energy harvesting circuit being electrically coupled to the first and second arcuate-shaped piezo-electric devices and receiving the first and second voltages, the energy harvesting circuit outputting a DC voltage in response to receiving the first and second voltages; and
an energy storage device being electrically coupled to the energy harvesting circuit and receiving the DC voltage.

17. The wearable power generating device of claim 16, further comprising:
a microprocessor being disposed on and coupled to the arcuate-shaped flexible substrate, the microprocessor being electrically coupled to the energy storage device;
a biometric sensor being disposed on and coupled to the arcuate-shaped flexible substrate, the biometric sensor being operably coupled to the microprocessor, the biometric sensor generating a second signal indicative of a biometric parameter level of a user; and
a display device being disposed on and coupled to the arcuate-shaped flexible substrate, the display device being operably coupled to the microprocessor, the microprocessor being programmed to generating a display command to induce the display device to display the biometric parameter level.

18. A wearable power generating device, comprising:
an arcuate-shaped flexible substrate;
a first arcuate-shaped piezo-electric device being disposed on and coupled to an outer surface of the arcuate-shaped flexible substrate that generates a first voltage in response to the first arcuate-shaped piezo-electric device being bent;
a second arcuate-shaped piezo-electric device being disposed on and coupled to the arcuate-shaped flexible substrate that generates a second voltage in response to the second arcuate-shaped piezo-electric device being bent, the second arcuate-shaped piezo-electric device being electrically coupled in series with the first arcuate-shaped piezo-electric device;
an energy harvesting circuit being disposed on and coupled to the outer surface of the arcuate-shaped flexible substrate, the energy harvesting circuit being electrically coupled to the first and second arcuate-shaped piezo-electric devices and receiving the first and second voltages, the energy harvesting circuit outputting a DC voltage in response to receiving the first and second voltages; and
an energy storage device being electrically coupled to the energy harvesting circuit and receiving the DC voltage.

19. The wearable power generating device of claim 18, wherein the first arcuate-shaped piezo-electric device has a uniform cross-sectional thickness.

20. The wearable power generating device of claim 18, further comprising:
a microprocessor being disposed on and coupled to the arcuate-shaped flexible substrate, the microprocessor being electrically coupled to the energy storage device;
a biometric sensor being disposed on and coupled to the arcuate-shaped flexible substrate, the biometric sensor being operably coupled to the microprocessor, the biometric sensor generating a second signal indicative of a biometric parameter level of a user, and
a display device being disposed on and coupled to the arcuate-shaped flexible substrate, the display device being operably coupled to the microprocessor, the microprocessor being programmed to generating a display command to induce the display device to display the biometric parameter level.

* * * * *